United States Patent [19]

Schwindeman et al.

[11] Patent Number: 5,626,798
[45] Date of Patent: May 6, 1997

[54] ARYLLITHIUM PRODUCTS AND PROCESSES

[75] Inventors: James A. Schwindeman, Lincolnton; Douglas E. Sutton, Kings Mountain; Robert C. Morrison, Gastonia; Sonia S. Stryker, Charlotte, all of N.C.

[73] Assignee: FMC Corporation, Philadelphia, Pa.

[21] Appl. No.: 587,813

[22] Filed: Jan. 5, 1996

[51] Int. Cl.$^6$ .................................................. C07F 1/02
[52] U.S. Cl. ............................................................. 260/665 R
[58] Field of Search ................................................ 260/665 R

[56] References Cited

U.S. PATENT DOCUMENTS

| | | | |
|---|---|---|---|
| 3,197,516 | 7/1965 | Esmay et al. | 260/665 |
| 3,446,860 | 5/1969 | Beumel | 260/665 |
| 3,452,112 | 6/1969 | Kamienski et al. | 260/665 R |
| 3,534,113 | 10/1970 | Eastham et al. | 260/665 R |
| 3,632,658 | 1/1972 | Halasa | 260/665 R |
| 4,354,982 | 10/1982 | Bogdanovic | 260/665 R |
| 5,211,888 | 5/1993 | Morrison et al. | 260/665 R |
| 5,340,507 | 8/1994 | Morrison et al. | 260/665 R |
| 5,523,447 | 6/1996 | Kamienski et al. | 260/665 R X |

FOREIGN PATENT DOCUMENTS

WO92/19622  11/1992  WIPO.

OTHER PUBLICATIONS

Gilman, Haubein and Hartzfeld, J. Org. Chem 19, 1034 (1954) The Cleavage of Some Ethers by Organolithium Compounds.

Gelman and Gaj, J. Org. Chem 22, 1165 (1957), Preparaion and Stability of Someorganolithium Compounds in Tetrahydrofuran.

Holding and Pletcher, Electrochim Acta (34)1529, (1989), A Chemical Approach to the Study of Films on Lithium in Organic Electrolytes for Batteries.

*Primary Examiner*—Paul F. Shaver
*Attorney, Agent, or Firm*—Bell, Seltzer, Park & Gibson, P.A.

[57] ABSTRACT

An improved process for producing high purity solutions of aryllithium compounds comprising reacting a particulate alkali metal having a particle size in the range of 10 to 300 microns, with an aryl halide in a normally liquid etheral solvent of the formula ROR$^1$, wherein R and R$^1$ are selected from the group of alkyl radicals containing from 3 to 6 carbon atoms, in the presence of a Lewis base compound selected from compounds of the formula: R$^2$AR$^3$(R$^4$)$_z$ and

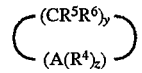

wherein A is selected from oxygen, nitrogen, phosphorus or sulfur; R$^2$, R$^3$, and R$^4$ are selected from alkyl radicals containing from 1 to 6 carbon atoms; R$^5$ and R$^6$ are independently selected from hydrogen or alkyl radicals containing one to six carbon atoms; y is an integer from 4 to 6; but when A is oxygen or sulfur, z is zero; and when A is nitrogen or phosphorus, z is one, and provided there is a mole ratio of ether to aryl halide of at least 1.3 to 1 and a mole ratio of Lewis base to aryl halide of from 0.01 to 0.50; and products of the process.

9 Claims, No Drawings

ARYLLITHIUM PRODUCTS AND PROCESSES

This invention concerns a process for producing aryllithium compounds and certain novel aryllithium compositions.

The preparation of aryllithium compounds by the direct reaction of an organic halide with lithium metal in an ethereal solvent is well known. Ethereal solvents are employed due to the insolubility of aryllithium compounds in purely hydrocarbon solvents. However, it is well known that aryllithium compounds react with ethers of low carbon number, e.g., ethyl ether, resulting in cleavage of the ether linkage and destruction of the aryllithium compound (Gilman, Haubein, and Hartzfield, *J. Org. Chem.*, 19, 1034 (1954); Gilman and Gag, *J. Org. Chem.*, 22, 1167 (1954); and Brawl, *Chem. Revs.*, 54, 615, (1954)).

U.S. Pat. Nos. 3,197,516 and 3,446,860 overcome the problems of lack of hydrocarbon solubility and stability in ethyl ether solutions by using mixed ether/hydrocarbon solvent reaction mediums that contain at least enough ethyl ether to solubilize the aryllithium. Generally, this constitutes about 25 volume percent or more of the total solvent employed. Thus, the high degree of flammability of the solution due to the presence of the highly volatile ethyl ether still persists. Many users and potential users of these solutions object to the presence of ethyl ether for this reason.

Patent WO92/19622 circumvented this problem by the use of longer chain dialkyl ethers containing from 6 to 10 carbon atoms, such as dibutyl ether. Although the aryllithium (e.g., phenyllithium) products resulting from the use of dibutyl ether as a solvent were indeed more stable, difficulties arose in the process due to the decreased Lewis basicity of this solvent. Thus, reactions between lithium metal and chlorobenzene decreased considerably during the last quarter of the halide feed. Because of this decrease, impurities such as biphenyllithium and biphenyl were formed, due to the occurrence of side reactions between the phenyllithium and chlorobenzene with a concurrent reduction in phenyllithium assay over extended periods of time.

A process has now been devised which promotes the completion of the aryl halide-metal reaction, significantly reducing the amount of unreacted aryl halide and impurities.

This invention provides an improved process for producing high purity, stable solutions of aryllithium compounds by reacting an alkali metal such as lithium metal with an aryl halide in an ethereal solvent of the formula $ROR^1$, wherein R and $R^1$ are selected from the group of alkyl radicals containing from 3 to 6 carbon atoms, in the presence of an added Lewis base compound of the formula: $R^2AR^3(R^4)_z$ or

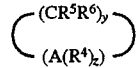

wherein A is selected from oxygen, nitrogen, phosphorus or sulfur; $R^2$, $R^3$, and $R^4$ are selected from alkyl radicals containing from 1 to 6 carbon atoms; $R^5$ and $R^6$ are independently selected from hydrogen or alkyl radicals containing one to six carbon atoms; y is an integer from 4 to 6; but when A is oxygen or sulfur, z is zero; and when A is nitrogen or phosphorus, z is one, and provided there is a mole ratio of ether to aryl halide of at least 1.3 to 1 and a mole ratio of Lewis base to aryl halide of from 0.01 to 0.50.

In accordance with the present invention, certain Lewis bases, such as ethers, sulfides, phosphines and tertiary amines, are added in small quantities to the reacting mixture of an aryl halide, such as chlorobenzene, and an alkali metal, such as lithium metal, in the form of a finely divided powder suspended in a medium of an dialkyl ether, such as dibutyl ether, exert a beneficial effect on the yield of aryllithium, such as phenyllithium, produced, the appearance of the solution, the amount of byproduct impurities, and especially, on the amount of unreacted aryl halide, such as chlorobenzene. It is important that the amount of aryl halide, such as chlorobenzene, be reduced as quickly as possible. When sizable quantities of post-feed chlorobenzene are allowed to persist for as long as 10–20 hours or even longer, yields of phenyllithium are drastically reduced and byproduct impurity levels are increased. As little as 1 mole percent or as much as 50 mole percent (based on the aryl halide) of these added Lewis bases can be employed with good results.

For example, when 5–10 mole percent of methyl tert-butyl ether (based on the starting chlorobenzene) is added to the halide to be fed to lithium metal powder suspended in dibutyl ether, unreacted halide levels drop to less than 5 mole % within 1–2 hours after halide addition is complete and drop to less than 1 mole % within 4–5 hours after halide addition is complete. With no added methyl tert-butyl ether, unreacted halide levels at the end of the feed are higher than 20 mole %, do not drop below the 5 mole level until 3 hours afterwards, and then persist at several mole % for many hours longer. WO 92/19622 gives no details about unreacted halide levels during the first several hours after halide addition is complete, but teaches stirring overnight to reduce halide values to zero.

Lewis base compounds useful in practicing the invention can be selected from the group represented by the formula $R^2AR^3(R^4)_z$, wherein $R^2$, $R^3$, $R^4$ and z have the meanings herein before ascribed, which include acyclic dialkyl ethers, dialkyl sulfides, trialkyl phosphines and trialkyl amines, such as, e.g., methyl tert-butyl ether, ethyl tert-butyl ether, dimethyl ether, diethyl ether, methyl tert-amyl ether, diethylsulfide, dibutylsulfide, methyl tert-butylsulfide, trimethylamine, triethylamine, methyldibutylamine, triisopropylphosphine and tributylphosphine.

Additional Lewis base compounds useful in practicing the invention can be selected from the group represented by the formula:

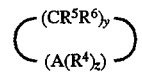

wherein $R^4$, $R^5$, $R^6$, y and z have the meanings herein before ascribed, which include, but are not limited to, cyclic ethers, sulfides, phosphines and amines, such as, e.g., tetrahydrofuran, 2-methyltetrahydrofuran, tetrahydropyran, 2-methyltetrahydropyran, tetrahydrothiophene, 2-methyltetrahydrothiophene, N-methylpyrrolidine, N-methylpiperidine and P-methyl cyclopentamethylenephosphine.

Other Lewis base compounds contemplated are those ethers and amines containing more than one heteroatom, such as, e.g., dioxane, ethylene glycol dimethyl ether, 1,4-dithane, 1,4-thioxane, N,N,N',N'-tetramethylethylenediamine, N,N-dimethylpiperazine, 1,4-diazobicyclo[2.2.2]octane, N-methylmorpholine and 1,2-bis-(dimethylphosphino)ethane.

These Lewis base compounds may be added directly to the lithium dispersion/solvent mixture prior to or anytime during the halide feed, or, they may be mixed with the halide feed and added continuously throughout the halide feed.

Normally liquid ether solvents useful in the practice of this invention are of the formula $ROR^1$ wherein R and $R^1$ are generally independently selected from alkyl groups containing at least 3 carbon atoms; R and $R^1$ can be the same or they can be different. Mixtures of ethers can, of course, be used. Typical ethers useful in practicing this invention include, but are not limited to, di-n-butyl ether, di-n-pentyl ether, di-n-propyl ether, and the like.

Alkali metal employed in this process should be in a finely divided state, preferably that produced by dispersing large pieces of the metal in a hydrocarbon oil above the melting point of the metal. Generally, the resulting dispersed particles of metal are in the range of 10 to 300 microns.

Reaction temperatures should be kept relatively low, i.e., below 40 degrees Centigrade, and preferably in the range of 25–35 degrees Centigrade.

Another aspect of this invention includes the compositions resulting from the novel process described above. Thus, this invention also includes novel, high purity, stable solutions of aryl alkali metal compounds such as aryllithium compounds produced by reacting, for example, lithium metal, with an aryl halide in an ethereal solvent of the formula $ROR^1$, wherein R and $R^1$ are selected from the group of alkyl radicals containing from 3 to 6 carbon atoms, in the presence of an added Lewis base of the formula $R^2AR^3(R^4)_z$ or

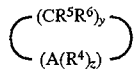

wherein A is selected from oxygen, nitrogen, phosphorus or sulfur; $R^2$, $R^3$, and $R^4$ are selected from alkyl radicals containing from 1 to 6 carbon atoms; $R^5$ and $R^6$ are independently selected from hydrogen or alkyl radicals containing one to six carbon atoms; y is an integer from 4 to 6; but when A is oxygen or sulfur, z is zero; and when A is nitrogen or phosphorus, z is one, and provided there is a mole ratio of ether to aryl halide of at least 1.3 to 1 and a mole ratio of Lewis base to aryl halide of from 0.01 to 0.50.

Numerous aryllithium compounds, other than phenyllithium, can be produced according to this novel process. These compounds are, for instance, biphenyllithiums, such as 2-biphenyllithium and 4-biphenyllithium, alpha-naphthyllithium, 2-lithotoluene, 4-lithiotoluene, 2-lithioanisole, and 4-dimethylaminophenyllithium.

The final product solutions are assayed for alkali metal content, such as aryllithium content, by total alkalinity titration and Watson Eastham titration for active carbon-bound lithium. The solutions are also analyzed for unreacted chlorobenzene by Gas Liquid Chromatography (GLC) analysis.

The process is conducted in an inert atmosphere to protect the aryllithium products which are degraded by contact with a reactive atmosphere, which is air containing any appreciable amounts of water vapor. The inert atmosphere is typically a noble gas and preferably argon or helium.

The following examples further illustrate the invention. Unless noted otherwise, all temperatures are in degrees Centigrade and the reactions conducted under an argon atmosphere.

EXAMPLE 1

Preparation of Phenyllithium Using 10 Mole % Methyl tert-Butyl Ether Based on Chlorobenzene (10162)

The following materials and equipment were employed: 8.67 grams (1.25 moles) of lithium powder containing 0.87% Na (based on lithium content); 58.59 grams (0.52 moles) of chlorobenzene; 121 grams (0.94 moles) of dibutyl ether used for reaction solvent; 35.8 grams (0.28 moles) of dibutyl ether used for washes of reaction muds; 4.6 grams (0.052 moles) of methyl tert-butyl ether; a round bottom, 500 milliliter, three-neck Morton reaction flask equipped with a mechanical stirrer and two Claisen adapters, one equipped with a thermocouple and a dry-ice condenser with a gas inlet and another equipped with a sample port and a pressure-equalizing dropping funnel; dry-ice/hexane cooling bath; and a medium porosity filter funnel.

All glassware was baked in an oven overnight at 125° C., assembled hot and purged with argon until cool.

To the reaction flask containing the lithium powder and dibutyl ether used for reaction was added, dropwise, over a period of sixty minutes, a solution of the chlorobenzene and methyl tert-butyl ether, while maintaining the reaction temperature between 30 and 35 degrees Centigrade. Samples of the reaction mixture were removed periodically, filtered, hydrolyzed, and assayed for unreacted chlorobenzene by gas chromatography (GLC). The following levels of unreacted chlorobenzene were found: at 15 minutes from start of halide feed, 19%; at 30 minutes, 31%; at 60 minutes (end of feed), 26%; at 120 minutes, 6%, and at 240 minutes, 1%. After filtration and washing of reaction muds, a clear, light amber solution was obtained, yield=173.57 grams, which assayed 22.30 weight percent phenyllithium by total alkalinity titration and 22.00 weight percent phenyllithium by Watson-Eastham active assay titration. The yield of phenyllithium based on the latter analysis was 87.4%.

COMPARATIVE EXAMPLES

Preparation of Phenyllithium In Dibutyl Ether Using No Added Lewis Base (10127)

The above experiment was repeated using the following quantities of materials: 9.13 grams (1.32 moles) of lithium powder; 129 grams (0.99 moles) of dibutyl ether for reaction, 34 grams (0.26 moles) of dibutyl ether for reaction mud washings; 61.69 grams (0.55 moles) of chlorobenzene. No methyl tert-butyl ether was added to the reaction.

The reaction was carried out as described above. Samples of the reaction mixture were removed periodically, filtered, hydrolyzed, and assayed for unreacted chlorobenzene by gas chromatography (GLC). The following were the amounts of unreacted chlorobenzene at various times. At 15 minutes from start of halide feed, 36%; at 30 minutes, 29%; at 60 minutes (end of the feed), 38%; at 120 minutes, 16%, and at 240 minutes, 9%. After filtration and washing of reaction muds, a clear, dark amber solution was obtained, yield= 180.57 grams, which assayed 20.97 weight percent phenyllithium by total alkalinity titration and 20.61 weight percent phenyllithium by Watson-Eastham active assay titration. The isolated yield of phenyllithium was 80.8%.

Two other experiments showed a much greater effect of unreacted chlorobenzene on the yield of phenyllithium when no Lewis base additive was employed.

| Expt. No. | Time post-feed (hrs) | Unreacted PhCl (%) |
| --- | --- | --- |
| 9577 | 1 | 29 |
| | 2 | 27 |
| | 3 | 25 |
| | 24 | 6 |
| 9655 | 1.5 | 18 |
| | 2.5 | 17 |
| | 4.5 | 16 |
| | 72 | 8 |

The yields in both experiments was 80%.

The above experiments show that there is a definite reduction in the amount of unreacted chlorobenzene present during the reaction when a Lewis base such as methyl tert-butyl ether is employed in the preparation of phenyllithium and a corresponding improvement in the yield.

EXAMPLE 2

Preparation of Phenyllithium Using 10 mole % Triethylamine Based on Chlorobenzene. (10061)

The following materials were employed: 12.5 grams (1.80 moles) of lithium powder; 84.46 grams (0.75 moles) of chlorobenzene; 176 grams (1.35 moles) of dibutyl ether used for reaction solvent; 51 grams (0.39 moles) of dibutyl ether used for washes of reaction muds, and 7.59 grams (0.075 moles) of triethylamine.

The equipment described in Experiment 1 was employed. To the reaction flask containing the lithium powder and dibutyl ether used for reaction was added, dropwise, over a period of ninety minutes, a solution of the chlorobenzene and triethylamine, while maintaining the reaction temperature between 30 and 35 degrees Centigrade. The progress of the reaction was monitored by GLC analysis. The reaction mixture was stirred for an additional 3 hours. The reaction mixture was filtered under argon pressure and the lithium chloride muds washed with fresh dibutyl ether. The combined filtrates weighed 263 grams, which assayed 23.46 weight percent phenyllithium by total alkalinity titration and 21.89 weight percent phenyllithium by Watson-Eastham active assay titration. The yield of phenyllithium based on the latter analysis was 91.5%.

EXAMPLE 3

Preparation of Phenyllithium Using 2 Mole % Tetrahydrofuran Based on Chlorobenzene. (10046)

The following materials were employed: 13.9 grams (2.00 moles) of lithium powder; 93.92 grams (0.83 moles) of chlorobenzene; 216 grams (1.66 moles) of dibutyl ether used for reaction solvent; 36 grams (0.28 moles) of dibutyl ether used for washes of reaction muds, and 1.23 grams (0.017 moles) of tetrahydrofuran.

The equipment described in Experiment 1 was employed. To the reaction flask containing the lithium powder and dibutyl ether used for reaction was added, dropwise, over a period of sixty-eight minutes, a solution of the chlorobenzene and tetrahydrofuran, while maintaining the reaction temperature between 30 and 35 degrees Centigrade. The progress of the reaction was monitored by GLC analysis. The reaction mixture was stirred for an additional 3 hours. The reaction mixture was filtered under argon pressure and the lithium chloride muds washed with fresh dibutyl ether. The combined filtrates weighed 282 grams, which assayed 22.50 weight percent phenyllithium by total alkalinity titration and 22.44 weight percent phenyllithium by Watson-Eastham active assay titration. The yield of phenyllithium based on the latter analysis was 90.4%.

We claim:

1. An improved process for producing high purity solutions of aryllithium compounds comprising reacting a particulate alkali metal having a particle size in the range of 10 to 300 microns, with an aryl halide in a normally liquid ethereal solvent of the formula $ROR^1$, wherein R and $R^1$ are selected from alkyl radicals containing from 3 to 6 carbon atoms, in the presence of a Lewis base compound selected from compounds of the formula: $R^2AR^3(R^4)_z$ and

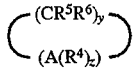

wherein A is selected from oxygen, nitrogen, phosphorus or sulfur; $R^2$, $R^3$, and $R^4$ are selected from alkyl radicals containing from 1 to 6 carbon atoms; $R^5$ and $R^6$ are independently selected from hydrogen or alkyl radicals containing one to six carbon atoms; y is an integer from 4 to 6; but when A is oxygen or sulfur, z is zero; and when A is nitrogen or phosphorus, z is one, and provided there is a mole ratio of ether to aryl halide of at least 1.3 to 1 and a mole ratio of Lewis base to aryl halide of from 0.01 to 0.50, wherein the ethereal solvent is different from the Lewis base compound.

2. The process of claim 1 wherein the aryl halide is chlorobenzene, the ethereal solvent is dibutyl ether, and the Lewis base is methyl tert-butyl ether.

3. The process of claim 2 wherein the mole ratio of dibutyl ether to chlorobenzene is 1.8 to 2.1 and the mole ratio of methyl tert-butyl ether to chlorobenzene is 0.05 to 0.15.

4. The process of claim 1 wherein the alkali metal is lithium.

5. An aryllithium composition consisting essentially of a solution of an alkali metal aryl compound, in a normally liquid ethereal solvent, wherein the molar ratio of solvent to alkali metal aryl compound is from 1.3 to 2.8 and the mole ratio of Lewis base to alkali metal aryl compound is from 0.01 to 0.50, the Lewis base being selected from compounds of the formulae $R^2AR^3(R^4)_z$ and

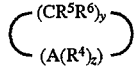

wherein A is selected from oxygen, nitrogen, phosphorus or sulfur; $R^2$, $R^3$, and $R^4$ are selected from alkyl radicals containing from 1 to 6 carbon atoms; $R^5$ and $R^6$ are independently selected from hydrogen or alkyl radicals containing one to six carbon atoms; y is an integer from 4 to 6; but when A is oxygen or sulfur, z is zero; and when A is nitrogen or phosphorus, z is one, wherein the ethereal solvent and the Lewis base are different.

6. The composition of claim 5 wherein the alkali metal compound is phenyllithium, the ethereal solvent is dibutyl ether and the Lewis base is methyl tert-butyl ether.

7. The composition of claim 6 wherein the molar ratio of phenyllithium to dibutyl ether is 1.8 to 2.1 and the mole ratio of methyl tert-butyl ether to phenyllithium is 0.05 to 0.15.

8. A process for producing high purity solutions of aryllithium compounds comprising reacting a particulate alkali metal having a particle size in the range of 10 to 300 microns with chlorobenzene in dibutyl ether solvent in the presence of a Lewis base methyl tert-butyl ether, provided there is a mole ratio of solvent to chlorobenzene of at least 1.3 to 1 and a mole ratio of Lewis base to chlorobenzene of from 0.01 to 0.50.

9. An aryllithium composition consisting essentially of a solution of phenyllithium in dibutyl ether solvent and in the presence of a Lewis base methyl tert-butyl ether, wherein the molar ratio of solvent to phenyllithium is from 1.3 to 2.8 and the mole ratio of Lewis base to phenyllithium is from 0.01 to 0.50.

* * * * *